US006462202B1

United States Patent
Schuhbauer et al.

(10) Patent No.: US 6,462,202 B1
(45) Date of Patent: Oct. 8, 2002

(54) METHOD FOR THE PRODUCTION OF A SOLVENT-FREE α-LIPONIC ACID

(75) Inventors: Hans Schuhbauer, Trostberg; Stefan Winkler, Obing; Ansgar Gruber, Altenmarkt, all of (DE)

(73) Assignee: Degussa AG, Trostberg (DE)

( * ) Notice: Subject to any disclaimer, the term of this patent is extended or adjusted under 35 U.S.C. 154(b) by 0 days.

(21) Appl. No.: 10/030,491

(22) PCT Filed: Aug. 10, 2000

(86) PCT No.: PCT/EP00/07802

§ 371 (c)(1),
(2), (4) Date: Oct. 25, 2001

(87) PCT Pub. No.: WO01/12620

PCT Pub. Date: Feb. 22, 2001

(30) Foreign Application Priority Data

Aug. 14, 1999 (DE) .......................................... 199 38 621

(51) Int. Cl.⁷ .............................................. C07D 339/04
(52) U.S. Cl. ......................................................... 549/39
(58) Field of Search ............................................ 549/39

(56) References Cited

FOREIGN PATENT DOCUMENTS

DE         197 26 519         12/1998

*Primary Examiner*—Bernard Dentz
(74) *Attorney, Agent, or Firm*—Fulbright & Jaworski L.L.P.

(57) ABSTRACT

Solvent-free α-lipoic acid is produced by dissolving
a) the α-lipoic acid to be purified in aqueous alkaline solution, or dissolving the salt thereof in water and adjusting an alkaline pH,
b) removing solid impurities present where appropriate from the aqueous solution from stage a),
c) adjusting the aqueous solution from stage a) or b) to a pH of from 1.0 to 5.0 with the aid of an acid and
d) isolating the precipitated α-lipoic acid by known methods.

This results in a solvent-free α-lipoic acid with improved chemical purity.

22 Claims, No Drawings

METHOD FOR THE PRODUCTION OF A SOLVENT-FREE α-LIPONIC ACID

This application is a 371 of PCT/EP00/07802 filed Aug. 10, 2000.

The present invention relates to a method for the production of solvent-free α-lipoic acid.

α-Lipoic acid (thioctic acid, 1,2-dithiolane-3-pentanoic acid) is a natural substance which occurs in the form of the R enantiomer in low concentrations in plant and animal cells. The physiological action of α-lipoic acid, which was originally discovered as a growth factor, in hydrophilic and lipophilic media is as a coenzyme of the oxidative decarboxylation of α-keto carboxylic acids (e.g. pyruvates) and as an antioxidant, and it is able to regenerate vitamin C, vitamin E, glutathione and coenzyme Q10. Racemic α-lipoic acid is approved for the treatment of liver disorders and neuropathies (e.g. diabetic poly-neuropathies); its use as an effective inhibitor of the replication of HIV-1 viruses has been suggested (cf. Klin. Wochenschr. 1991, 69(15), 722–724). The racemate of α-lipoic acid also displays cytoprotective, antiinflammatory and antinociceptive (analgesic) properties, and it has emerged for the pure optical isomers of α-lipoic acid (R-α-lipoic acid and S-α-lipoic acid) that, in contrast to the racemate, the R enantiomer shows a predominantly antiinflammatory, and the S enantiomer shows a predominantly anti-nociceptive, profile of actions (cf. EP 0 812 590 A2).

The syntheses of crude racemic α-lipoic acid and of enantiopure R- or S-α-lipoic acid takes place by known methods or ones analogous thereto, as described or summarized, for example, in Crévisy et al., Eur. J. Org. Chem. 1998, 1949, Fadnavis et al., Tetrahedron Asym. 1998, 9, 4109, Dhar et al., J. Org. Chem. 1992, 57, 1699, Adger et al., J. Chem. Soc. Chem. Commun. 1995, 1563, Dasaradhi et al., J. Chem. Soc. Chem. Commun. 1990, 729, Gopalan et al., J. Chem. Soc. Perkin Trans. I 1990, 1897, Yadav et al., J. Sci. Ind. Res. 1990, 49, 400, Tolstikov et al., Bioorg. Khim. 1990, 16, 1670, Gopalan et al., Tetrahedron Lett. 1989, 5705.

The usual method for purifying crude α-lipoic acid is recrystallization from solvents (e.g. from n-pentane, cyclohexane, methylcyclohexane, ethyl acetate) or mixtures of solvents (e.g. from ethyl acetate and hexane), as recommended, for example, in Brookes et al., J. Chem. Soc. Perkin Trans. 1 1988, 9, Segre et al., J. Am. Chem. Soc. 1957, 3503, Walton et al., J. Am. Chem. Soc. 1955, 77, 5144, Acker et al., J. Am. Chem. Soc. 1954, 76, 6483. The crystallized α-lipoic acid is then filtered or centrifuged and subsequently dried by conventional methods. The crystalline α-lipoic acid obtained in this way, which, however, contains residues of solvent, is finally processed further to the finished drug product.

An alternative additional method for purifying lipoic acid which has previously been recrystallized by a mixture of cyclohexane and ethyl acetate is, as proposed in DE 197 26 519 A1, a treatment of the crude material enriched in lipoic acid with liquid or supercritical carbon dioxide. Nevertheless, even the purified lipoic acid obtained in this way still has residual solvent contents of from 8 to 1030 ppm cyclohexane and 83 to 225 ppm ethyl acetate. In addition, the described method of treatment with liquid or supercritical carbon dioxide under a pressure in the range from 50 to 1000 bar is complicated and can be carried out only if appropriate safety measures are complied with.

As has emerged, residual solvent contents in α-lipoic acid resulting from the production process cannot be completely precluded. According to the 4th International Conference on Harmonization (ICH 4), in the production of active ingredients for medicinal products, however, certain solvents must either be entirely avoided (class 1 solvents: with known or strongly suspected human carcinogenicity, with environment-endangering properties), or be limited to protect patients from possible adverse reactions (class 2 solvents: with non-genotoxic carcinogenicity in animals, with irreversible toxicity or reversible but significant toxicity). Where possible, less toxic solvents (class 3) should be used. This classification is moreover by no means exhaustive, and it is just as possible for new scientific findings about recommended limits to appear as for the classification of particular solvents to change. For example, there are tendencies to reduce even further the limit for the residual solvent content in α-lipoic acid for medical approvals. Medicinal active ingredients and products ought never to contain residual solvent contents exceeding limits relevant to safety. However, even noncritical solvents such as, for example, acetic acid, which is permitted as food additive, may have an unpleasant effect on the odor or taste of an active ingredient or medicinal product. Since a residual solvent content cannot have therapeutic benefits, these solvents should generally be avoided as far as possible (or removed where appropriate) in order to comply with the requirements of GMP (Good Manufacturing Practice), product specifications and other quality characteristics. Suitable guidelines within the framework of the abovementioned ICH 4 are various policies, e.g. guideline Q3A, Impurities in New Active Substances; Q3B, Impurities in New Medicinal Products.

The present invention is therefore based on the object of designing a method for the production of solvent-free α-lipoic acid not having the disadvantages of the known methods but making it possible to produce, in a simple manner, α-lipoic acid which no longer contains any residual organic solvents.

This object has been achieved according to the invention by
a) dissolving the α-lipoic acid to be purified in aqueous alkaline solution, or dissolving the salt thereof in water and adjusting an alkaline pH,
b) removing any solid impurities present from the aqueous solution from stage a),
c) adjusting the aqueous solution from stage a) or b) to a pH of from −1.0 to 5.0 with the aid of an acid and
d) isolating the precipitated α-lipoic acid by known methods.

It has surprisingly emerged in this connection that not only is a solvent-free α-lipoic acid obtained in this way but, in addition, typical impurities from the production process, such as, for example, 1,2,3-tri-thiane-4-valeric acid (6,8-epithioctic acid), are removed and thus the chemical purity of α-lipoic acid is improved.

In the method of the invention, the α-lipoic acid to be purified is dissolved in stage a) in aqueous alkaline solution expediently having a pH of from 7.5 to 16.0, preferably from 9.0 to 14.0. The alkaline solution may contain conventional bases in the form of hydroxides, carbonates and bicarbonates of alkali metals or alkaline earth metals (such as, for example, sodium, potassium, calcium and magnesium), ammonia or primary, secondary or tertiary amines (such as, for example, benzylamine, diisopropylamine, triethylamine).

The crude α-lipoic acid employed in stage a) may in this connection have been produced by any method. The α-lipoic acid may, for example, be produced by recrystallization using an organic solvent, or be crude α-lipoic acid in the absence of organic solvents.

It is likewise possible to employ in the method of the invention both racemic α-lipoic acid and an enantiopure R-(+)-α-lipoic acid or S-(−)-α-lipoic acid or any mixtures thereof. In place of free α-lipoic acid it is also possible for a salt of α-lipoic acid to be dissolved in water and subsequently made alkaline, e.g. with the bases already described, expediently to a pH of from 7.5 to 16.0, preferably 9.0 to 14.0

In a preferred embodiment, alkali metal (such as, for example, sodium or potassium) or alkaline earth metal salts (such as, for example, calcium or magnesium) of α-lipoic acid are used thereby. However, it is also possible to employ other salts of α-lipoic acid, in which case their cations may consist, in particular, of elements zinc, iron, copper, palladium, vanadium and selenium. It is also possible to employ as starting compounds salts of α-lipoic acid with organic cations such as, for example, open-chain or cyclic ammonium compounds (such as, for example, ammonium, methyl-ammonium, benzylmethylammonium or tetramethylammonium cations), complex cations (with metallic central atoms such as, for example, iron(III), chromium(III) or cobalt(II) and neutral, cationic or anionic ligands (such as, for example, water ($H_2O$), ammonia ($NH^3$), carbonyl (CO), cyano (CN) or nitroso (NO)) or oxo cations (such as, for example, oxovanadium(V) ($VO_2^+$) or oxovanadium(IV) ($VO^{2+}$)).

The content of α-lipoic acid in stage a) may vary within wide limits. However, it has proved to be advantageous to adjust the concentration of α-lipoic acid in the aqueous alkaline solution to 0.01 to 15% by weight, preferably to 0.1 to 5% by weight.

In a preferred embodiment, activated carbon is added in an amount of from 0.01 to 50% by weight, based on the α-lipoic acid equivalents in the solution, to the aqueous alkaline solution in stage a) before stage b) is carried out. It is additionally possible with the aid of these activated carbons to remove interfering impurities, by-products and/or residual solvent. Examples of activated carbons which have proved to be particularly advantageous are Norit SX Plus, Norit Pureflow 1, Norit Pureflow C or Norit SA Plus.

In the following stage b) any solid impurities present are removed from the aqueous solution from stage a). The usual methods such as filtration, centrifugation and the like are suitable.

The aqueous solution from stage a) or b) is adjusted in the following stage c) to a pH of from −1.0 to 5.0, preferably from 1.0 to 4.0, with the aid of an acid. This is essential to the invention. Both inorganic and organic acids can be employed for adjusting the pH. From the group of inorganic acids those which have proved to be particularly satisfactory are the customary mineral acids such as, for example, hydrohalic acid (in the form of hydrochloric acid or hydrobromic acid), nitric acid, sulfuric acid and phosphoric acid. The pH can also be adjusted with organic acids such as, for example, an aliphatic carboxylic acid having 1 to 6 carbon atoms (e.g. formic acid, acetic acid), an aromatic carboxylic acid (e.g. benzoic acid), a halogenated or oxygenated carboxylic acid (e.g. chloroacetic acid, trifluoroacetic acid, pyruvic acid) or an aliphatic or aromatic sulfonic acid (e.g. methanesulfonic acid, toluenesulfonic acid). The acidification causes the α-lipoic acid to precipitate.

The temperature in stages a) to c) is not critical but is expediently chosen in the range from −50 to +60° C. with room temperatures being preferred.

In the subsequent stage d), the lipoic acid precipitated by adjusting the pH is removed, preferably by filtration or centrifugation. The temperature in stage d) is expediently chosen in the range from −50 to +60° C., preferably in the range from −10 to +10° C.

The purified α-lipoic acid resulting from stage d) contains as sole additional component the physiologically completely acceptable solvent water. The storage stability of moist, semimoist or dry α-lipoic acid is not impaired by the water content. If required, the water content of the purified and dried α-lipoic acid can be reduced to values of <0.5, in particular <0.1, % by weight by conventional drying, for example in a fluidized-bed dryer, paddle dryer, conical screw mixing dryer or double cone mixing dryer.

Organic solvents are no longer detectable in the α-lipoic acid produced by the method of the invention. The detection and quantitation limits for a number of conventional organic solvents which may be employed in the production and/or purification of α-lipoic acid are summarized by way of example in Table 1 below.

TABLE 1

Detection limits and quantitation limits of organic solvents

| Solvent | Detection limit | Quantitation limit |
|---|---|---|
| Acetonitrile | 10 ppm | 50 ppm |
| Cyclohexane | 1.2 ppm | 4 ppm |
| Dichloromethane | 7.6 ppm | 25 ppm |
| Ethanol | 5.3 ppm | 25 ppm |
| Ethyl acetate | 5.7 ppm | 19 ppm |
| Methanol | 11 ppm | 38 ppm |
| Methyl acetate | 1.6 ppm | 5 ppm |
| Methyl tertiary butyl ether | 10 ppm | 20 ppm |
| Toluene | 5.8 ppm | 19 ppm |

The method of the invention thus represents a considerable improvement in the area of the purification of racemic or enantiopure α-lipoic acid because the quality requirements for active pharmaceutical ingredients and medicinal products are fully taken into account through complete removal of all traces of residual solvent.

The following examples are intended to explain the invention in detail.

EXAMPLES

The residual solvent content is measured by dissolving the resulting α-lipoic acid (about 1 g) in 10 ml of p-chlorotoluene, and injecting an aliquot of this solution directly into a gas chromatograph. Detection takes place by FID (flame ionization detection) using an external standard. The detection and quantitation limits are summarized in Table 1.

Example 1

30 kg of commercial racemic α-lipoic acid recrystallized from a mixture of ethyl acetate and cyclohexane and having a residual solvent content of 1.2% by weight after drying in a paddle dryer was introduced into 1000 l of water at 20° C. A pH of 9.0 was adjusted with 50% strength aqueous sodium hydroxide solution. This dilute aqueous solution was filtered through a 2 μ filter and, at 0° C., brought to a pH of 1.0 [lacuna] 5% strength aqueous hydrochloric acid. The precipitated α-lipoic acid was separated from the mother liquor in a centrifuge and washed with water until the washing water had a neutral pH. After drying in a paddle dryer (35° C., 5 mbar, 15 h), the standard parameters of an analysis of the product were measured (Table 2).

Example 2

20 kg of racemic α-lipoic acid recrystallized from a mixture of ethyl acetate and cyclohexane and having a residual solvent content of 1.2% by weight after drying in a paddle dryer was introduced into 1000 l of water at 20° C. A pH of 9.0 was adjusted with 50% strength aqueous sodium hydroxide solution, and then 1.0 kg of activated carbon of the Norit Pureflow 1 type were added. This dilute aqueous solution was filtered through a 2 μ filter and, at room temperature, brought to a pH of 2.0 with 15% strength aqueous hydrochloric acid. The precipitated α-lipoic acid was separated from the mother liquor in a centrifuge and washed with water until the washing water had a neutral pH. After drying in a paddle dryer (35° C., 5 mbar, 15 h), the standard parameters of an analysis of the product were measured (Table 2).

Example 3

30 kg of racemic α-lipoic acid from a chemical synthesis was introduced into 1000 l of water at 40° C. A pH of 13.0 was adjusted with aqueous sodium hydroxide solution, and then 1.0 kg of activated carbon of the Norit Pureflow 1 type was added. This dilute aqueous solution was filtered through a 2 μ filter and brought to a pH of 2.0 with 15% strength aqueous hydrochloric acid at 40° C. The precipitated α-lipoic acid was removed from the mother liquor in a centrifuge and washed with water until the washing water had a neutral pH. After drying in a paddle dryer (40° C., 5–10 mbar, 15 h), the standard analytical parameters of the product were measured (Table 2).

TABLE 2

Analytical parameters for crude and purified lipoic acid of Examples 1 to 3

| α-Lipoic acid | m.p. | Contents[1] | Impurities[1,2] | $H_2O$[3] | Residual solvent[4] | |
|---|---|---|---|---|---|---|
| Example 1: crude lipoic acid | 59.6–61.3° C. | 99.0% | <1.0% | 0.5% | $CH_2Cl_2$:<br>Ethanol:<br>MTBE:<br>unknown: | 880 ppm<br>540 ppm<br>650 ppm<br>590 ppm[5] |
| Example 1: pure lipoic acid | 60.1–61.1° C. | 99.1% | <1.0% | 0.1% | Acetonitrile:<br>Cyclohexane:<br>$CH_2Cl_2$:<br>Ethanol:<br>Ethyl acetate:<br>Methanol:<br>Methyl acetate:<br>MTBE:<br>Toluene: | n.d.<br>n.d.<br>n.d.<br>n.d.<br>n.d.<br>n.d.<br>n.d.<br>n.d.<br>n.d. |
| Example 2: crude lipoic acid | 60.3° C. | 96.9% | <1.0% | 0.5% | Cyclohexane:<br>Ethyl acetate: | 2950 ppm<br>420 ppm |
| Example 2: pure lipoic acid | 60.5–61.7° C. | 99.7% | <1.0% | 0.1% | Acetonitrile:<br>Cyclohexane:<br>$CH_2Cl_2$:<br>Ethanol:<br>Ethyl acetate:<br>Methanol:<br>Methyl acetate:<br>MTBE:<br>Toluene: | n.d.<br>n.d.<br>n.d.<br>n.d.<br>n.d.<br>n.d.<br>n.d.<br>n.d.<br>n.d. |
| Example 3: crude lipoid acid | 60.0–61.0° C. | 96.5% | <1.0% | 0.3% | Cyclohexane:<br>Methanol:<br>Toluene: | 550 ppm<br>120 ppm<br>335 ppm |
| Example 3: pure lipoic acid | 60.4–61.5° C. | 99.9% | <1.0% | 0.05% | Acetonitrile:<br>Cyclohexane:<br>$CH_2Cl_2$:<br>Ethanol:<br>Ethyl acetate:<br>Methanol<br>Methyl acetate:<br>MTBE:<br>Toluene: | n.d.<br>n.d.<br>n.d.<br>n.d.<br>n.d.<br>n.d.<br>n.d.<br>n.d.<br>n.d. |

[1]by HPLC
[2]e.g. 6,8-epilipoic acid
[3]by Karl-Fischer titration
[4]n.d. = not detectable
[5]unassigned solvent peak, evaluated as cyclohexane

What is claimed is:

1. A method for the production of solvent-free α-lipoic acid, comprising
   a) dissolving the α-lipoic acid to be purified in aqueous alkaline solution or dissolving α-lipoic acid salts in water and adjusting to an alkaline pH;
   b) removing any solid impurities present from the aqueous solution from stage a),
   c) adjusting the aqueous solution from stage a) or b) to a pH of from −1.0 to 5.0 with an acid to precipitate α-lipoic acid; and
   d) removing the precipitated α-lipoic acid.

2. The method of claim 1, wherein said α-lipoic acid is at least one of a racemic α-lipoic acid, an enantiopure R-(+)-α-lipoic acid or S-(−)-α-lipoic acid or mixtures thereof is employed.

3. The method of claim 1, wherein the aqueous alkaline solution in stage a) has an α-lipoic acid content of from 0.01 to 15.0% by weight.

4. The method of claim 1, wherein said alkaline solution comprises at least one base selected from the group consisting of hydroxides, carbonates, bicarbonates of alkali metals, bicarbonates of alkaline earth metals, ammonia, primary amines, secondary amines and tertiary amines.

5. The method of claim 1, wherein said α-lipoic acid is an alkali metal or alkaline earth metal salt of α-lipoic acid.

6. The method of claim 1, wherein the salts of α-lipoic acid comprise cations selected from the group consisting of zinc, iron, copper, palladium, vanadium and selenium.

7. The method of claim 1, wherein the α-lipoic acid salts is an organic cation.

8. The method of claim 7, wherein said organic cation is selected from the group consisting of open-chain ammonium compounds, cyclic ammonium compounds, complex cations and oxo cations.

9. The method of claim 1, wherein the pH in stage a) ranges from 7.5 to 16.0.

10. The method of claim 9, wherein pH in stage a) ranges from 9.0 to 14.0.

11. The method of claim 1, wherein activated carbon is added in an amount of from 0.01 to 50% by weight, based on the α-lipoic acid equivalents in the solution, to the aqueous alkaline solution in stage a) before stage b) is carried out.

12. The method of claim 1, wherein any solid impurities present in stage b) are removed by filtration.

13. The method of claim 1, wherein the pH in stage c) is adjusted by adding a mineral acid selected from the group of hydrohalic acid, nitric acid, sulfuric acid and phosphoric acid.

14. The method of claim 13, wherein said mineral acid is selected from the group consisting of hydrochloric acid and hydrobromic acid.

15. The method of claim 1, wherein in stage c) the pH is adjusted by addition of an acid, an aliphatic carboxylic acid having 1 to 6 carbon atoms, an aromatic carboxylic acid, a halogenated carboxylic acid, oxygenated carboxylic acid, an aliphatic sulfonic acid and an aromatic sulfonic acid.

16. The method of claim 1, wherein the precipitated α-lipoic acid is removed in stage d) by filtration or centrifugation.

17. The method of claim 1, wherein stages a) to c) are carried out at temperatures of from −50 to +60° C.

18. The method of claim 1, wherein stages a) to c) are conducted at room temperature.

19. The method of claim 1, wherein stage d) is carried out at temperatures of from −50 to +40° C.

20. The method of claim 19, wherein stage d) is carried out at a temperature in the range from −10 to +10° C.

21. The method of claim 1, wherein the α-lipoic acid is dried after stage d) to a water content is <0.5% by weight.

22. The method of claim 1, wherein the α-lipoic acid is dried to a water content of <0.1% by weight.

* * * * *